(12) United States Patent
Sauer et al.

(10) Patent No.: US 10,835,233 B2
(45) Date of Patent: Nov. 17, 2020

(54) SUTURING BACKSTOP FOR MINIMALLY INVASIVE SURGERY

(71) Applicant: LSI Solutions, Inc., Victor, NY (US)

(72) Inventors: Jude S. Sauer, Pittsford, NY (US); Angelo John Martellaro, Victor, NY (US)

(73) Assignee: LSI Solutions, Inc., Victor, NY (US)

( * ) Notice: Subject to any disclaimer, the term of this patent is extended or adjusted under 35 U.S.C. 154(b) by 736 days.

(21) Appl. No.: 15/242,049

(22) Filed: Aug. 19, 2016

(65) Prior Publication Data

US 2017/0049440 A1    Feb. 23, 2017

Related U.S. Application Data

(60) Provisional application No. 62/207,843, filed on Aug. 20, 2015.

(51) Int. Cl.
*A61B 17/04* (2006.01)
*A61F 2/24* (2006.01)
(Continued)

(52) U.S. Cl.
CPC ........ *A61B 17/0469* (2013.01); *A61F 2/2409* (2013.01); *A61B 2017/00349* (2013.01);
(Continued)

(58) Field of Classification Search
CPC .............. A61F 2/2409; A61B 17/0469; A61B 2017/00349; A61B 2017/0472;
(Continued)

(56) References Cited

U.S. PATENT DOCUMENTS

| 5,431,666 A | 7/1995 | Sauer |
| 5,562,686 A | 10/1996 | Sauer |
(Continued)

FOREIGN PATENT DOCUMENTS

| WO | WO 2004103157 A2 * | 12/2004 | ......... A61B 1/00071 |
| WO | WO 2014052599 A1 * | 4/2014 | ......... A61B 17/0401 |

OTHER PUBLICATIONS

Jan. 1, 2003 Product Literature; LSI Solutions® Sew-Right SR.5™, The Single Squeeze Suturing Device™.
(Continued)

*Primary Examiner* — Shaun L David
(74) *Attorney, Agent, or Firm* — David J. Gervasi; Christopher B. Miller

(57) ABSTRACT

A suturing backstop is disclosed. The suturing backstop has a suturing device receiver configured to receive at least a portion of a tissue bite area of a suturing device. The suturing backstop also has a sewing cuff receptacle. The suturing backstop further has one or more needle guides adjacent the sewing cuff receptacle. The suturing backstop also has one or more alignment stops configured to position said portion of the tissue bite area within the suturing device receiver such that when a needle from the suturing device is extended from a retracted to an engaged position, the needle passes through the sewing cuff receptacle and through a corresponding one of the one or more needle guides. A related method for placing sutures into a sewing cuff of a prosthetic replacement device is also disclosed.

7 Claims, 18 Drawing Sheets

(51) Int. Cl.
*A61B 17/00* (2006.01)
*A61B 17/06* (2006.01)
(52) U.S. Cl.
CPC ............... *A61B 2017/0472* (2013.01); *A61B 2017/0495* (2013.01); *A61B 2017/0608* (2013.01); *A61B 2017/06042* (2013.01)
(58) Field of Classification Search
CPC .. A61B 2017/0495; A61B 2017/06042; A61B 2017/0608
See application file for complete search history.

(56) References Cited

U.S. PATENT DOCUMENTS

| | | | | |
|---|---|---|---|---|
| 5,766,183 | A | 6/1998 | Sauer | |
| 6,368,334 | B1 | 4/2002 | Sauer | |
| 6,533,796 | B1 | 3/2003 | Sauer | |
| 6,997,931 | B2 | 2/2006 | Sauer | |
| 7,211,093 | B2 | 5/2007 | Sauer | |
| 7,407,505 | B2 | 8/2008 | Sauer | |
| 7,731,727 | B2 * | 6/2010 | Sauer | A61B 17/0057 606/139 |
| 8,313,496 | B2 * | 11/2012 | Sauer | A61B 1/00071 600/104 |
| 8,398,657 | B2 | 3/2013 | Sauer | |
| 8,652,149 | B2 | 2/2014 | Sauer | |
| 2002/0107530 | A1 | 8/2002 | Sauer | |
| 2004/0068272 | A1 | 4/2004 | Sauer | |
| 2005/0165419 | A1 | 7/2005 | Sauer | |
| 2007/0255296 | A1 | 11/2007 | Sauer | |
| 2009/0222027 | A1 | 9/2009 | Sauer | |
| 2009/0312772 | A1 * | 12/2009 | Chu | A61B 17/0469 606/144 |
| 2010/0211083 | A1 | 8/2010 | Sauer | |
| 2011/0118758 | A1 | 5/2011 | Sauer | |
| 2012/0016383 | A1 | 1/2012 | Sauer | |
| 2015/0282805 | A1 * | 10/2015 | Sauer | A61B 17/0469 606/145 |

OTHER PUBLICATIONS

Jan. 1, 2007 Product Literature; LSI Solutions® RD Technology Guide.
Oct. 3, 2009 Product Literature; LSI Solutions® RD Running Device™ Surgery'S Best Suturing Technology™.
May 11, 2011 Product Literature; LSI Solutions® Sew-Right SR.5™ Device and SR.5™ Quick Load™ Inservice Guide.
Jun. 16, 2016 Symposium; Knight, Peter, for Presentation At the STS 2011 Annual Meeting—Automated Remote Transapical Wound Closure System: Fresh Porcine Heart Bursting Pressure Study and Cadaver Endoscopic Demonstration.
Jun. 21, 2010 Symposium; Leigh, H. , for Presentation At the STS 2011 Annual Meeting—Fresh Porcine Heart Bursting Pressure Study Fig. 1.

* cited by examiner

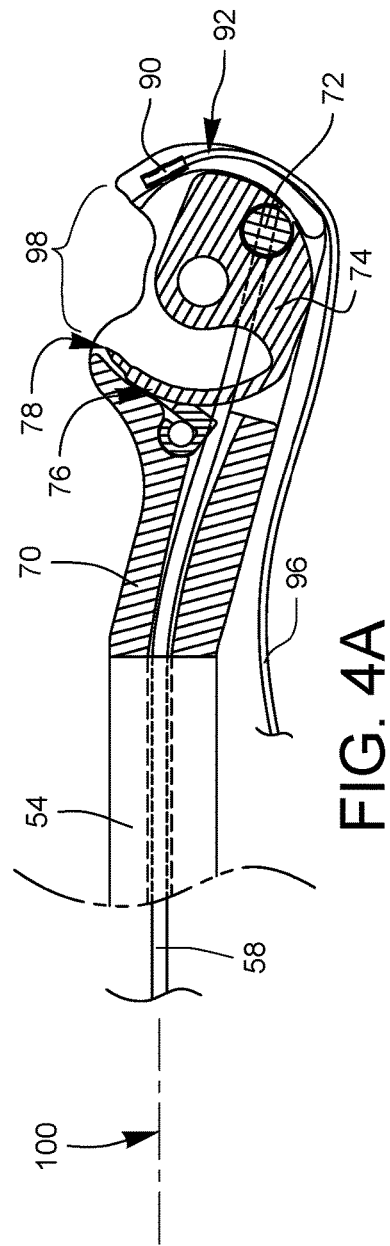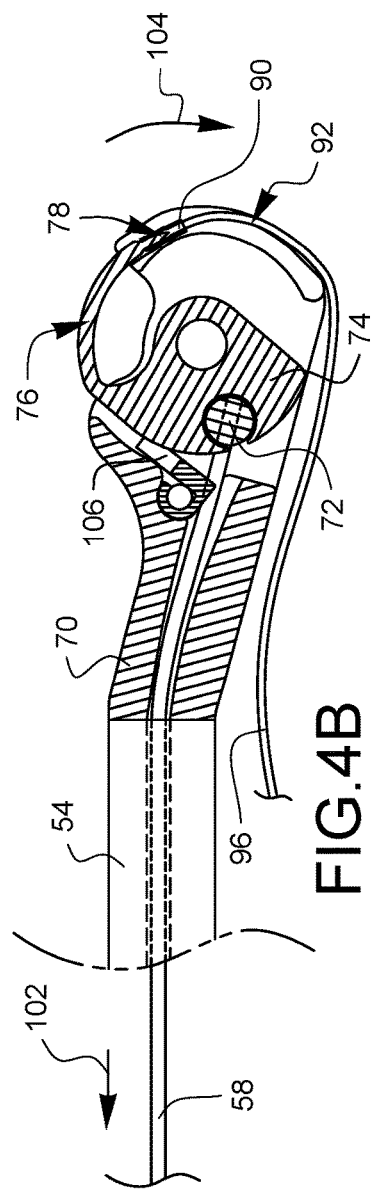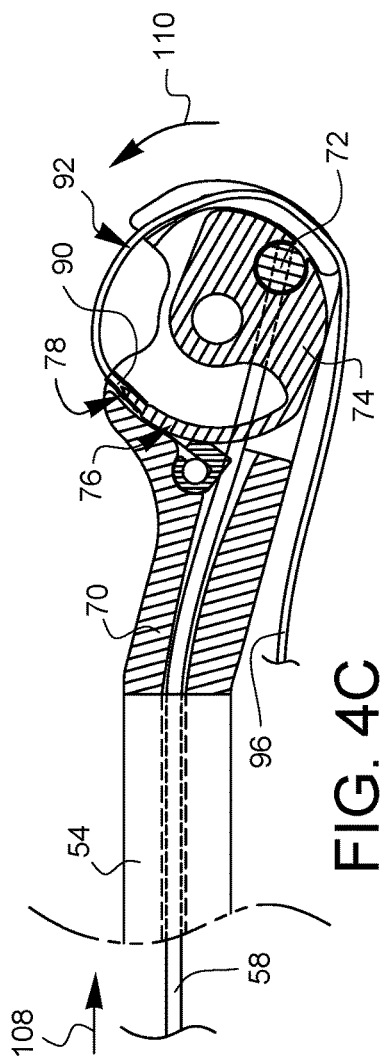

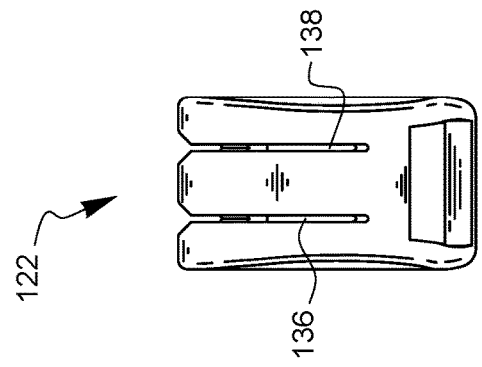
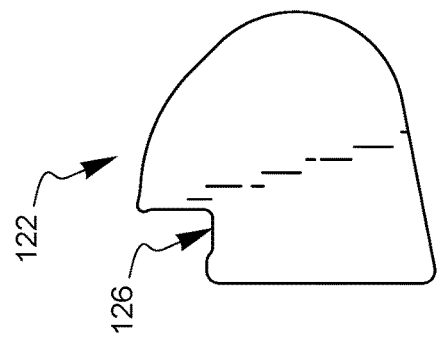
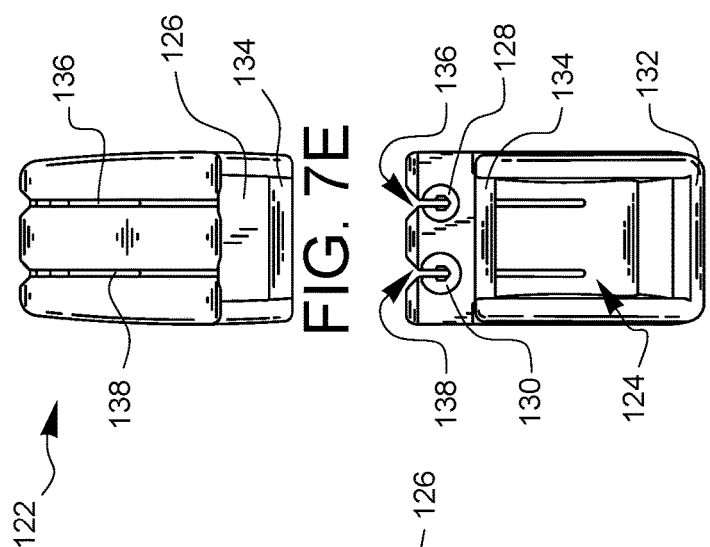
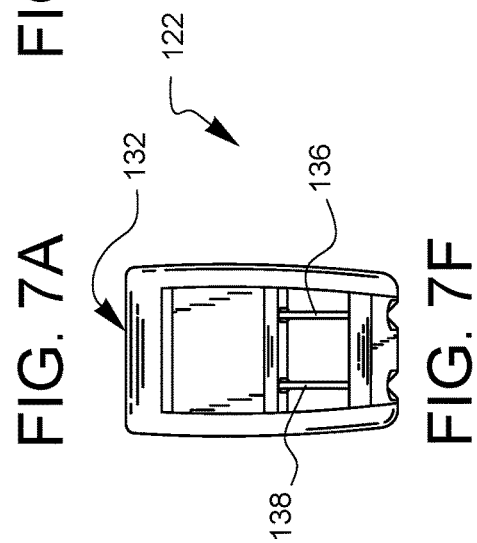
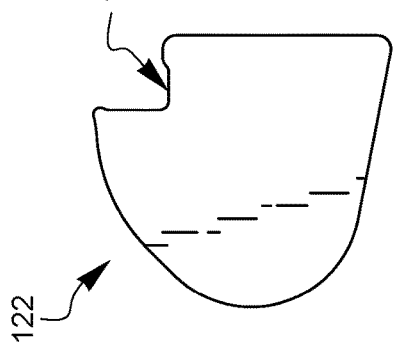

SUTURING BACKSTOP FOR MINIMALLY INVASIVE SURGERY

RELATED APPLICATION

This patent application claims priority to U.S. Provisional Patent Application No. 62/207,843 filed Aug. 20, 2015 and entitled "SUTURING BACKSTOP FOR MINIMALLY INVASIVE SURGERY". The 62/207,843 application is hereby incorporated by reference in its entirety.

FIELD

The claimed invention relates to minimally invasive surgical suturing, and more specifically to a backstop for minimally invasive surgery for the installation of a prosthetic device having a sewing cuff.

BACKGROUND

The human heart relies on a series of one-way valves to help control the flow of blood through the chambers of the heart. For example, referring to FIG. 1, deoxygenated blood returns to the heart 20, via the superior vena cava 22 and the inferior vena cava 24, entering the right atrium 26. The heart muscle tissue contracts in a rhythmic, coordinated heartbeat, first with an atrial contraction which aids blood in the right atrium 26 to pass through the tricuspid valve 28 and into the right ventricle 30. Following atrial contraction, ventricular contraction occurs and the tricuspid valve 28 closes. Ventricular contraction is stronger than atrial contraction, assisting blood flow through the pulmonic valve 32, out of the heart 20 via the pulmonary artery 34, and to the lungs (not shown) for oxygenation. Following the ventricular contraction, the pulmonic valve 32 closes, preventing the backwards flow of blood from the pulmonary artery 34 into the heart 20.

Oxygenated blood returns to the heart 20, via the pulmonary veins 36, entering the left atrium 38. Left atrial contraction assists blood in the left atrium 38 to pass through the mitral valve 40 and into the left ventricle 42. Following the atrial contraction, ensuing ventricular contraction causes mitral valve 40 closure, and pushes oxygenated blood from the left ventricle 42 through the aortic valve 44 and into the aorta 46 where it then circulates throughout the body. Under nominal conditions, prolapse of mitral valve 40 is prevented during ventricular contraction by chordae 40A attached between the mitral valve 40 leaflets and papillary muscles 40B. Following left ventricular contraction, the aortic valve 44 closes, preventing the backwards flow of blood from the aorta 46 into the heart 20.

Unfortunately, one or more of a person's heart valves 28, 32, 40, and 44 can have or develop problems which adversely affect their function and, consequently, negatively impact the person's health. Generally, problems with heart valves can be organized into two categories: regurgitation and/or stenosis. Regurgitation occurs if a heart valve does not seal tightly, thereby allowing blood to flow back into a chamber rather than advancing through and out of the heart. This can cause the heart to work harder to remain an effective pump. Regurgitation is frequently observed when the mitral valve 40 fails to properly close during a ventricular contraction. Mitral regurgitation can be caused by chordae 40A stretching, tearing, or rupturing, along with other structural changes within the heart.

Neochordal replacement for stretched or torn chordae is one option to reduce regurgitation. In such a procedure, chords to be replaced are identified and dissected as required. A papillary suture is placed in a papillary muscle corresponding to the dissected chord. The papillary suture may optionally be pledgeted on one or both sides of the papillary muscle. A leaflet suture is also placed in the corresponding mitral valve leaflet. The papillary suture and the leaflet suture may then be tied or otherwise fastened together to create a replacement chord to help support the mitral valve leaflet and prevent regurgitation.

Regurgitation with the mitral valve or the aortic valve may also occur when the valve's leaflets are unable to coapt properly. In such a situation, if the leaflets are still viable, surgeons may determine that the improper coaption is caused by changes in the surrounding annulus tissue whereby the annulus has become distorted due to disease or patient genetics/aging. One possible treatment in such situations is a valve annuloplasty, whereby a device (typically a ring) is sutured around the heart valve to help pull the valve leaflets together.

In cases of stenosis, when a heart valve does not fully patent due to stiff or fused leaflets, blood flow tract narrowing, or obstructive material buildup (e.g., calcium), installation of a replacement heart valve may be more appropriate. In these situations, the diseased heart valve may be removed and then a replacement valve may be sutured into the surrounding tissue.

Unfortunately, while many of the above techniques are proven methods of heart valve repair, there remains a need to make the procedures more efficient to reduce surgeon fatigue, shorten operating times, and reduce patient time on cardio-pulmonary bypass.

SUMMARY

A suturing backstop is disclosed. The suturing backstop has a suturing device receiver configured to receive at least a portion of a tissue bite area of a suturing device. The suturing backstop also has a sewing cuff receptacle. The suturing backstop further has one or more needle guides adjacent the sewing cuff receptacle. The suturing backstop also has one or more alignment stops configured to position said portion of the tissue bite area within the suturing device receiver such that when a needle from the suturing device is extended from a retracted to an engaged position, the needle passes through the sewing cuff receptacle and through a corresponding one of the one or more needle guides.

Another suturing backstop is disclosed. The suturing backstop has a suturing device receiver configured to receive at least a portion of a tissue bite area of a suturing device. The suturing backstop also has a sewing cuff receptacle. The suturing backstop further has one or more needle guides adjacent the sewing cuff receptacle.

A method of placing sutures into a sewing cuff of a prosthetic replacement valve is also disclosed. A suturing device tip is inserted into a suture backstop. The sewing cuff is set into a sewing cuff receptacle of the suture backstop. One or more needles of the suturing device are engaged so that each needle tip of the one or more needles pass through the sewing cuff, through one or more corresponding needle guides of the suture backstop, and into contact and coupling with one or more corresponding ferrules held in the suturing device. The one or more needles are retracted so that each needle tip coupled to a ferrule is pulled back through the one or more corresponding needle guides and the sewing cuff along with one or more corresponding suture ends which are coupled to the one or more corresponding ferrules.

BRIEF DESCRIPTION OF THE DRAWINGS

FIGS. 4A-4C are side partial cross-sectional views of the device tip of the surgical suturing device of FIG. 2 illustrating a suturing sequence.

FIGS. 7A, 7B, 7C, 7D, 7E, and 7F are front, left, right, back, top, and bottom elevational views, respectively, of the suturing backstop from FIG. 6A.

Figure 1:
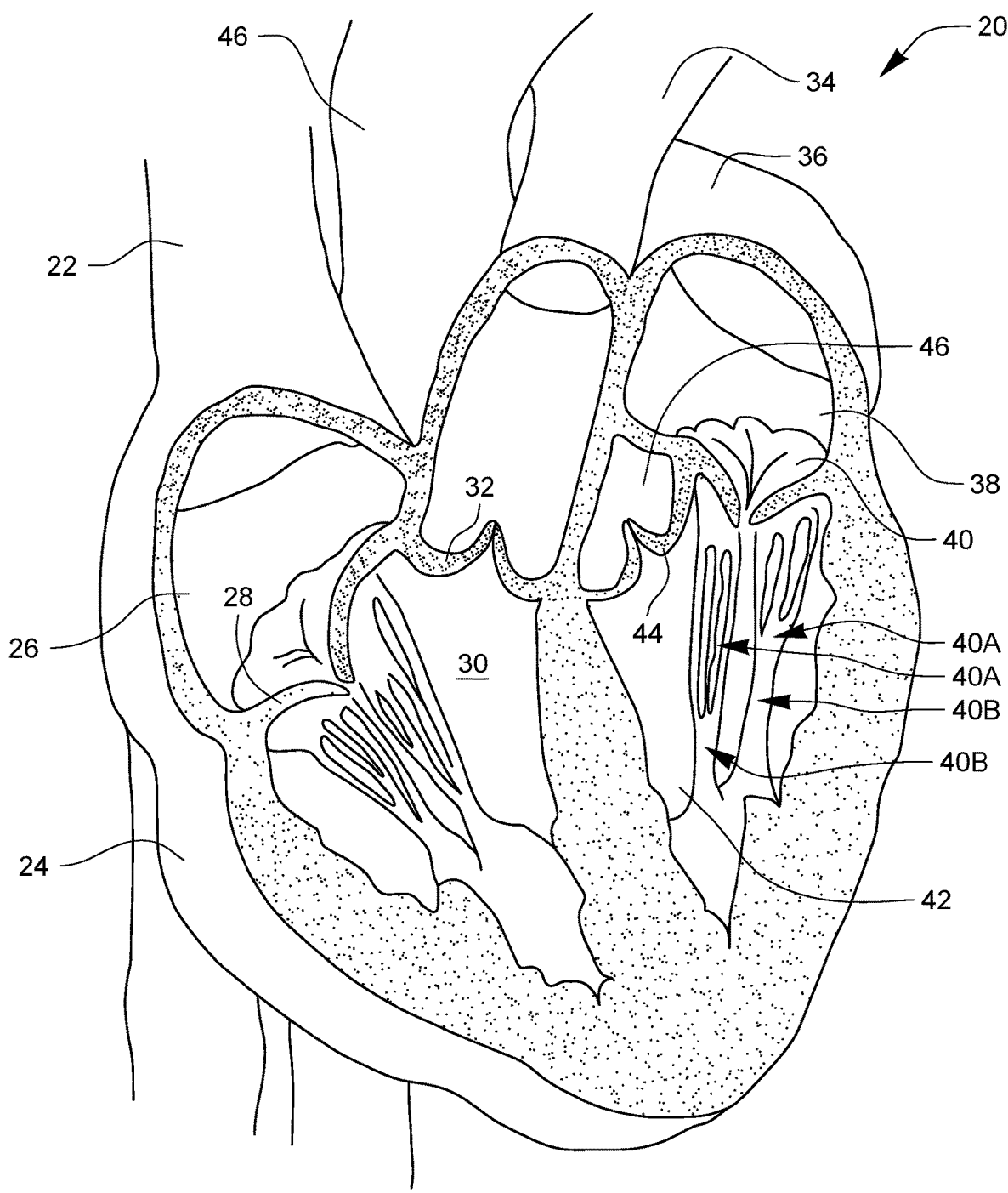
FIG. 1 is an illustration of a heart.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

Figure 2:
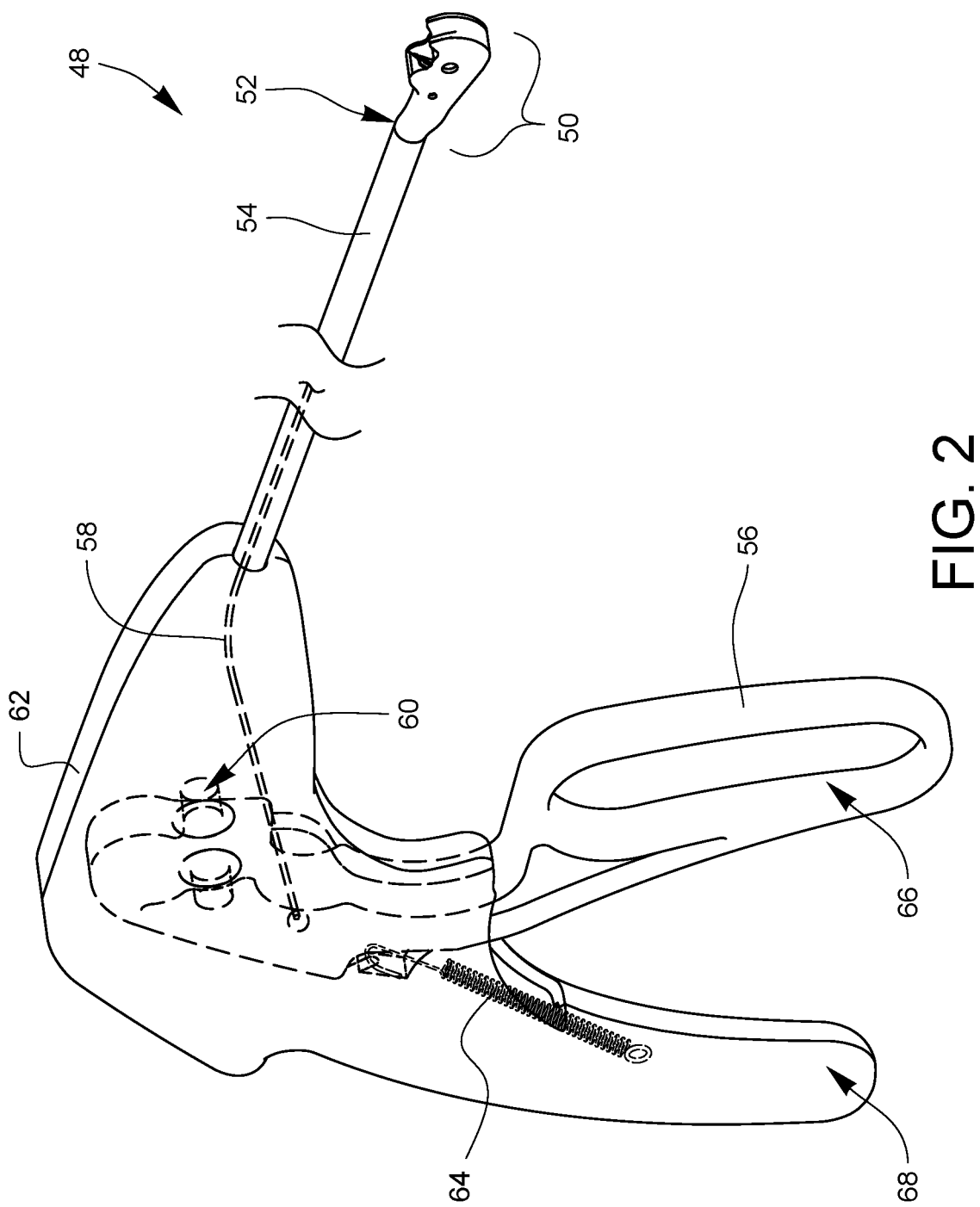
FIG. 2 is a perspective view of one embodiment of a surgical suturing device.

FIG. 2 is a perspective view of a surgical suturing device 48. The surgical suturing device 48 has a device tip 50 which is located at a distal end 52 of a shaft 54 and which will be discussed in more detail below. The surgical suturing device 48 also has an actuator 56 which is coupled to an actuator rod 58. The actuator 56 has an actuator pivot point 60 supported by a housing 62. An actuator spring 64 is coupled between the actuator 56 and the housing 62 to bias the actuator 56 into a retracted position, such as the position shown in FIG. 2. In this embodiment, a handle 66 of the actuator 56 is configured to be moved from the retracted position of FIG. 2 to an engaged position where the actuator 56 is pivoted around the pivot point 60 to move the handle 66 closer to a grip 68 of the housing 62. Since the point where the actuator rod 58 couples to the actuator 56 is between the handle 66 and the pivot point 60 in this embodiment, the actuator rod 58 will move proximally, away from the device tip 50 when the handle 66 is squeezed towards the grip 68. Conversely, in this embodiment, the actuator rod 58 will move distally, toward the device tip 50, when the handle 66 is moved away from the grip 68. Although the actuator 56 in this embodiment includes a lever, other embodiments may utilize a variety of other actuators, including, but not limited to, a control knob, a control wheel, a solenoid, a slider, a screw, one or more gears, one or more pulleys, a motor, or any plurality and/or combination thereof.

Figure 3:
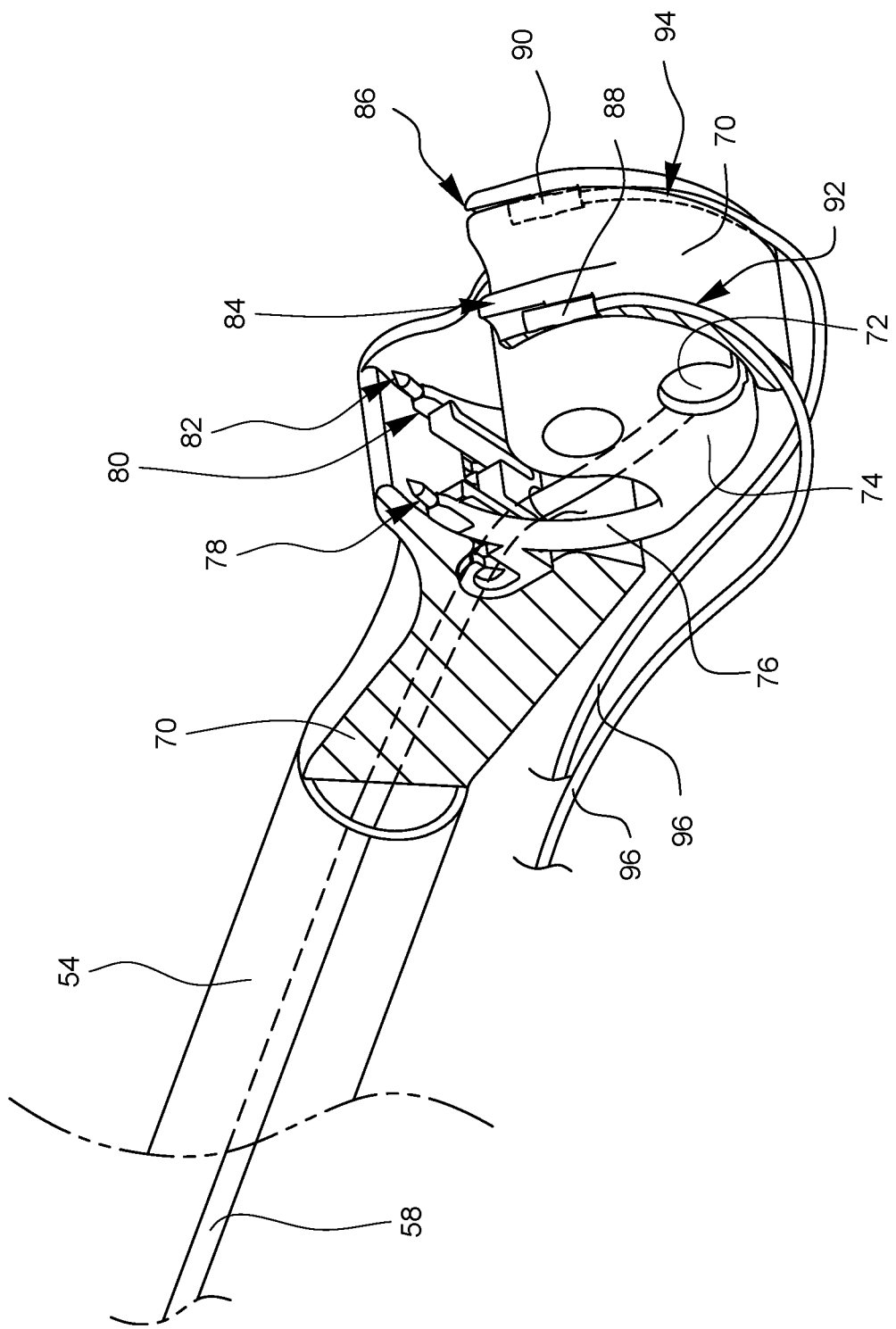
FIG. 3 is a partially exposed perspective view of the device tip of the surgical suturing device of FIG. 2.

FIG. 3 is a partially exposed perspective view of the device tip 50 from FIG. 2. FIG. 4A corresponds to FIG. 3 and is a partially cross-sectioned side view of the device tip 50 from FIG. 2. In FIG. 3, the needle 74 is shown in a retracted position, where the first ferrule engaging tip 78 and the second ferrule engaging tip 82 start away from their respective first and second ferrule holders 84, 86. The ferrule holders 84, 86 are either formed from or coupled to the device head 70. A first ferrule 88 and a second ferrule 90 are each installed in and held by respective first and second ferrule holders 84, 86. The first ferrule 88 is coupled to a first end 92 of a suture 96, while the second ferrule 90 is coupled to a second end 94 of the suture 96. The suture 96 may be of a variety of lengths, and for convenience the portion of the suture 96 where it loops back on itself is not shown. It should be understood that the term "suture", as used herein, is intended to cover any thread, cable, wire, filament, strand, line, yarn, gut, or similar structure, whether natural and/or synthetic, in monofilament, composite filament, or multi-filament form (whether braided, woven, twisted, or otherwise held together), as well as equivalents, substitutions, combinations, and pluralities thereof for such materials and structures.

The head 70 defines a tissue bite area 98. In this embodiment, as can be better seen in FIG. 4A, the tissue bite area 98 faces a direction which is substantially oblique to a longitudinal axis 100 of the shaft 54.

As shown in FIG. 4B, the actuator rod 58 may be moved in a proximal direction 102, which will cause the needle 74 to rotate in a first direction 104 about its needle pivot axis. While rotating in this first direction 104, the ferrule engaging tips 78, 82 of the curved arms 76, 80 pass from their retracted position (shown in FIGS. 3, 4A), through the tissue bite area 98, and to an engaged position (shown in FIG. 4B). In this embodiment, the ferrule engaging tips 78, 82 move along an arcuate path from a proximal side of the head 70 towards a distal end of the head 70. In the engaged position of FIG. 4B, the ferrule engaging tips 78, 82 are each coupled to corresponding ferrules 88, 90 by an interference fit or alternate attachment mechanism, the choice of which is known to those skilled in the art. This coupling of the ferrule engaging tips with the corresponding ferrules may be referred to as operational alignment.

As shown in FIG. 4C, the actuator rod 58 may be moved in a distal direction 108, which will cause the needle 74 to rotate in a second direction 110 (opposite the first direction 104) about its needle pivot axis. While rotating in this second direction 110, the ferrule engaging tips 78, 82 of the curved arms 76, 80 (and the ferrules 88, 90 which are coupled to them) pass from their engaged position (shown in FIG. 4B), back through the tissue bite area 98, and to the retracted position as shown in FIG. 4C. In this embodiment, while moving back to the retracted position, the ferrule engaging tips 78, 82 move along an arcuate path from the distal end of the head 70 to the proximal side of the head 70.

Depending on the embodiment, if a ferrule release feature 106 is present in the device, the ferrule release feature 106 may have elements which are positioned to ride against the curved arms, up the release ramps of the curved arms, and against the ferrules 88, 90 to remove the ferrules 88, 90 from the ferrule engaging tips 78, 82 when the tips 78, 82 return to the retracted position. In other embodiments, the actuator may be configured to selectively rotate the needle 74 past the retracted position, away from the engaged position, when desired, in order then to force the captured ferrules 88, 90 to engage the ferrule release feature 106. Some embodiments may not include a ferrule release feature at all.

Figure 5A:
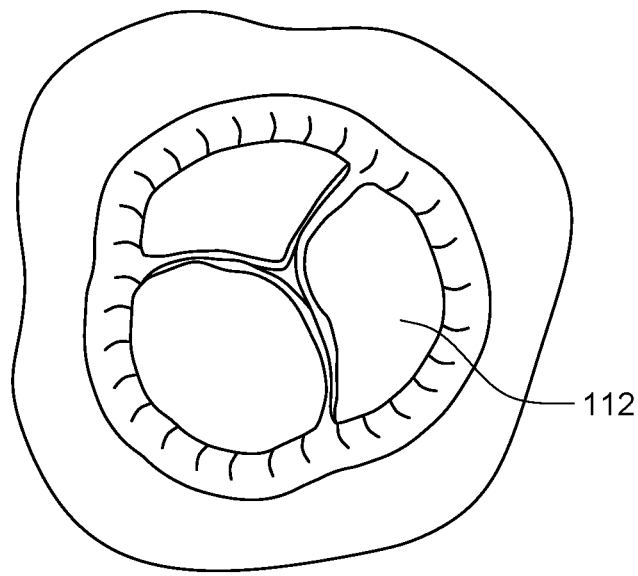
FIGS. 5A-5G illustrate a method of using an embodiment of the surgical suturing device from FIG. 2 to place a pledgeted suture in a valve annulus which has had its diseased valve leaflets removed.
Figure 5B:
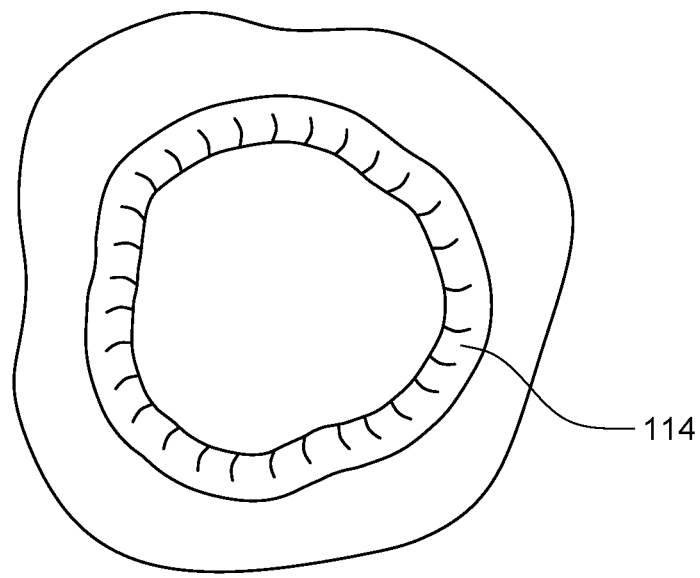
Figure 5C:
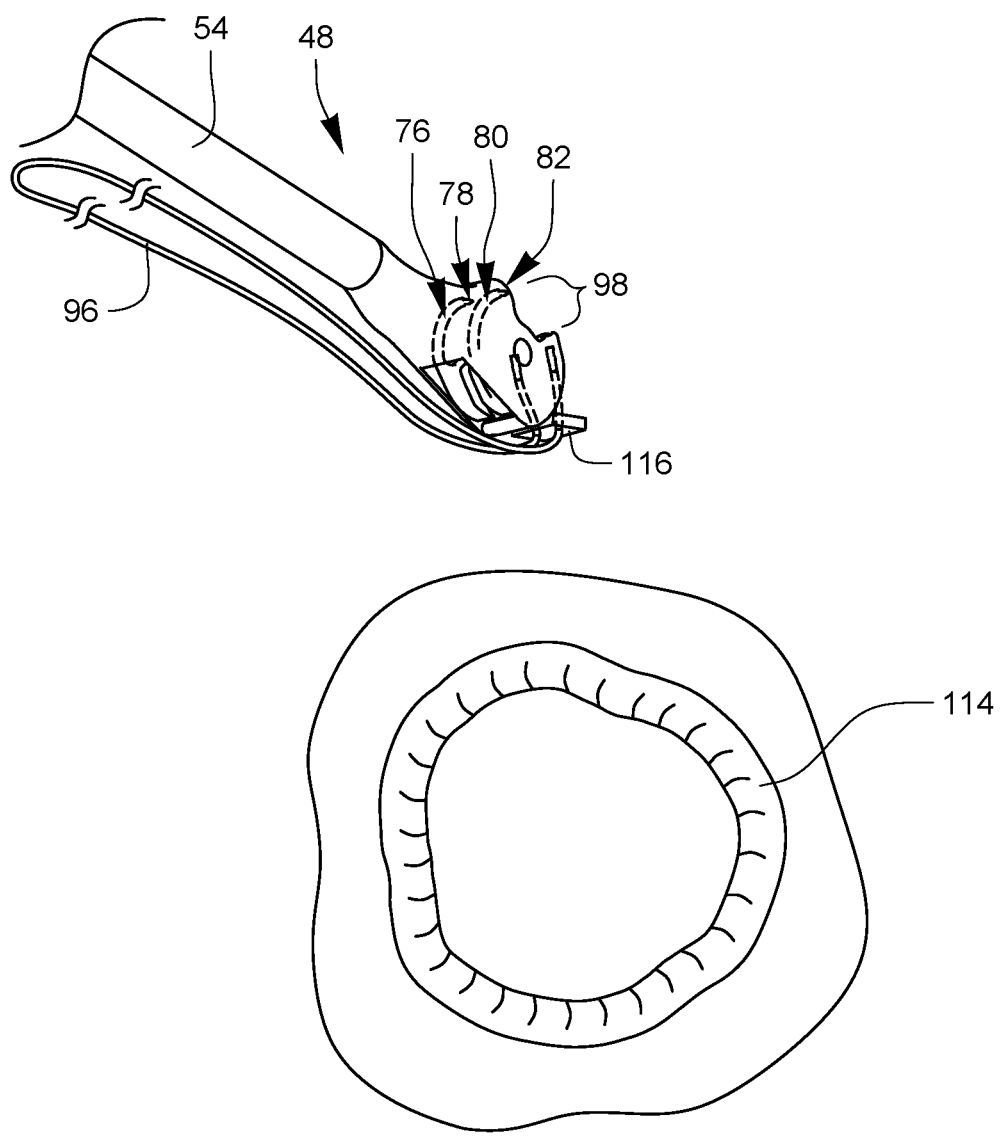

FIGS. 5A-5G illustrate a method of using an embodiment of the surgical suturing device from FIG. 2 to place a pledgeted suture in a valve annulus which has had its diseased valve leaflets removed. FIG. 5A schematically illustrates a diseased heart valve 112 in need of replacement. As a first action, a surgeon might gain access to the diseased valve 112 and dissect the leaflets of the valve, leaving the annulus 114 in preparation for installation of a replacement heart valve as shown in FIG. 5B. As illustrated in FIG. 5C, the suturing device 48 is ready to be used. For convenience, the handle, actuator, and entire shaft are not shown in these views. As before, the device 48 has a tissue bite area 98 defined at least in part by the head 70 at the end of the shaft 54. First and second ferrules 88, 90, coupled to the ends of suture 96 are held in ferrule holders on the distal side of the tissue bite area 98 in the device head 70. The first and second curved arms 76, 80 and their respective first and second ferrule engaging tips 78, 82 are in a retracted position on the proximal side of the tissue bite area 98. In this embodiment, the suture 96 is also pledgeted with a pledget 116 pre-installed on the suture 96.

Figure 5D:
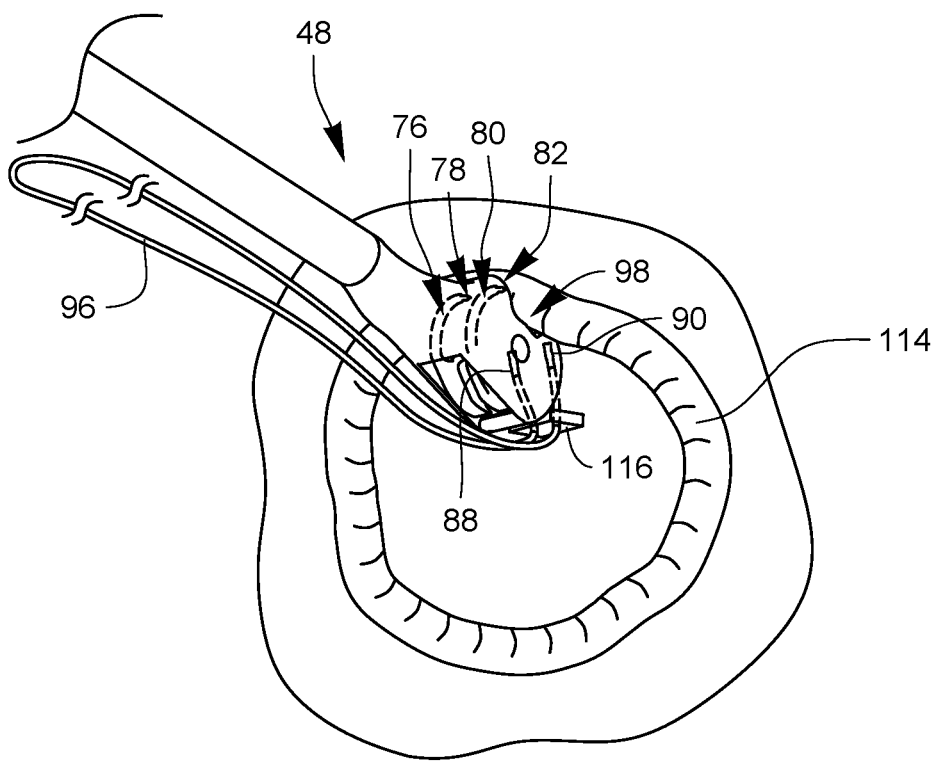

In this example, it would be desirable to attach the replacement heart valve to the remaining annulus 114. Therefore, as illustrated in FIG. 5D, the tissue bite area 98 of the surgical suturing device 48 could be placed over a portion of the annulus 114 where it would be desired to make some attachment stitches.

Figure 5E:
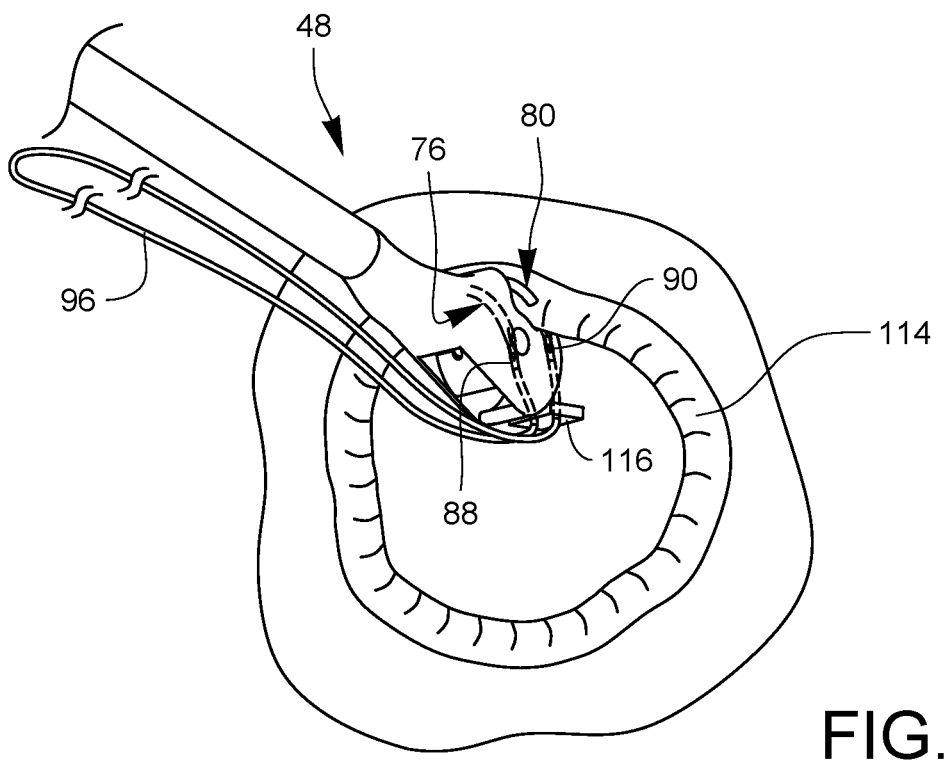
Figure 5F:
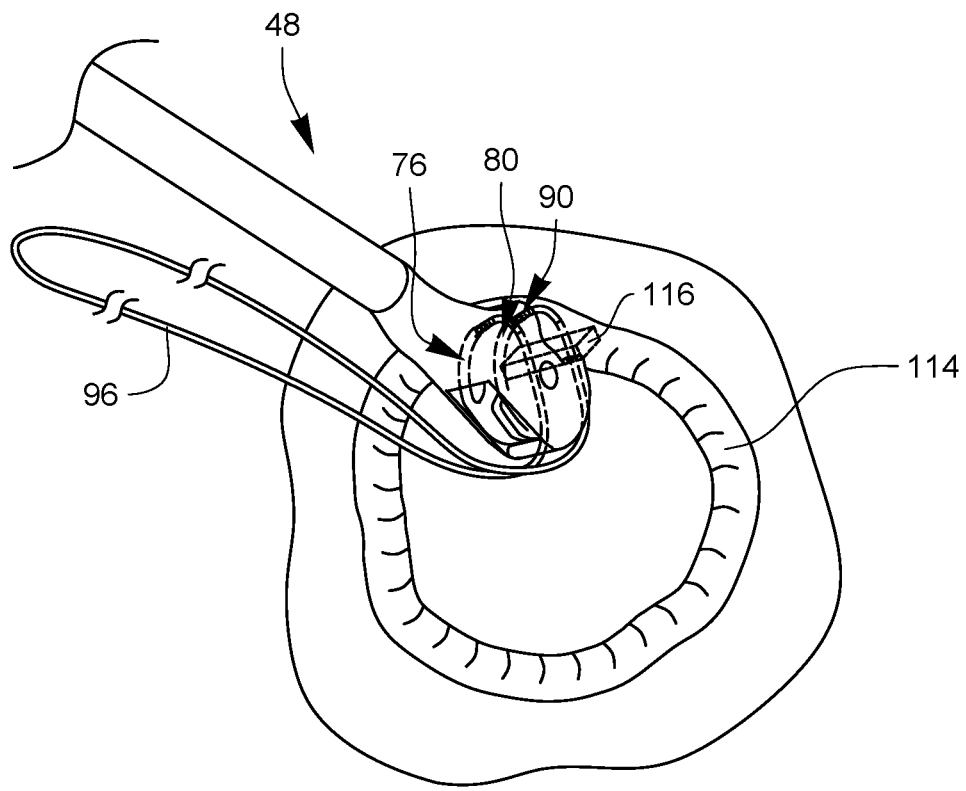
Figure 5G:
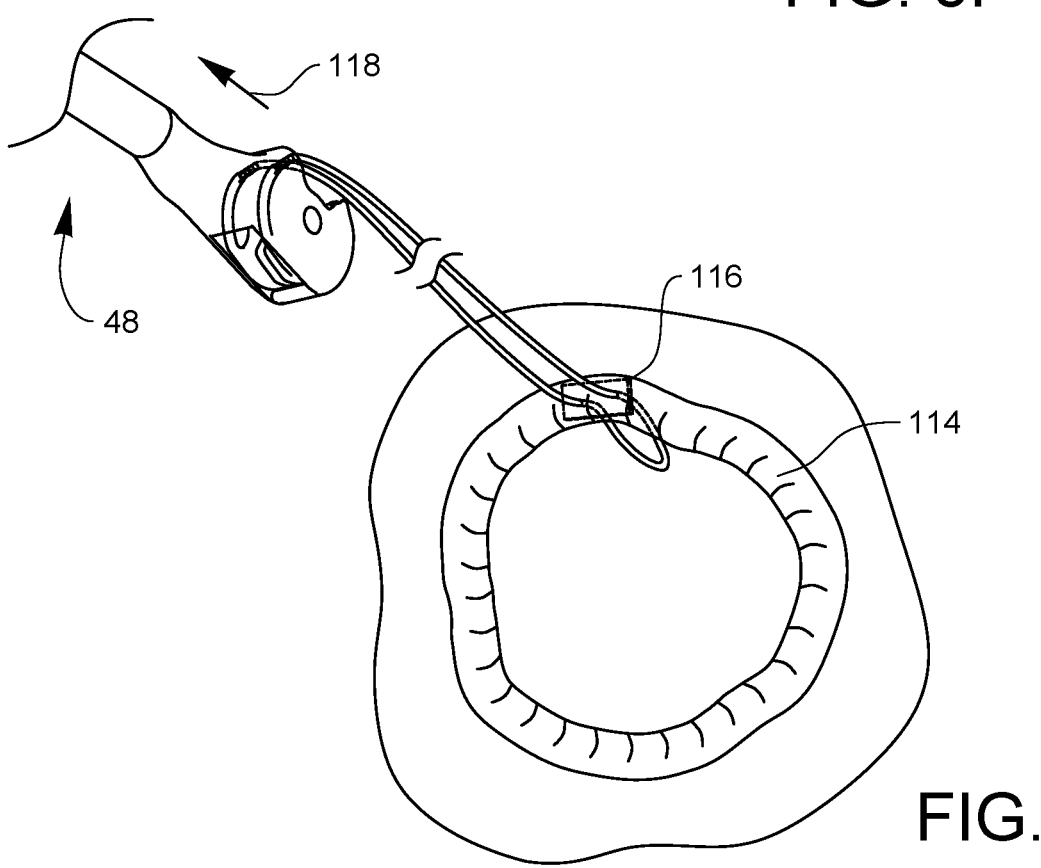

As shown in FIG. 5E, the needle is actuated so that the first and second curved arms 76, 80, and their respective ferrule engaging tips, pass through the annulus 114 in the tissue bite area and engage the corresponding first and second ferrules 88, 90. As shown in FIG. 5F, the needle is then reverse-actuated so that the first and second curved arms 76, 80 and their respective ferrule engaging tips and the respective ferrules 88, 90 held by those ferrule engaging tips are pulled back through the annulus 114 in the tissue bite area and into a retracted position again. Since the ends of suture 96 are coupled to the ferrules 88, 90, the suture 96 is also pulled through the annulus 114. The device 48 can be pulled back 118 to tighten a portion of the suture 96 against the pledget 116, and ultimately against the annulus 114.

Figure 5H:
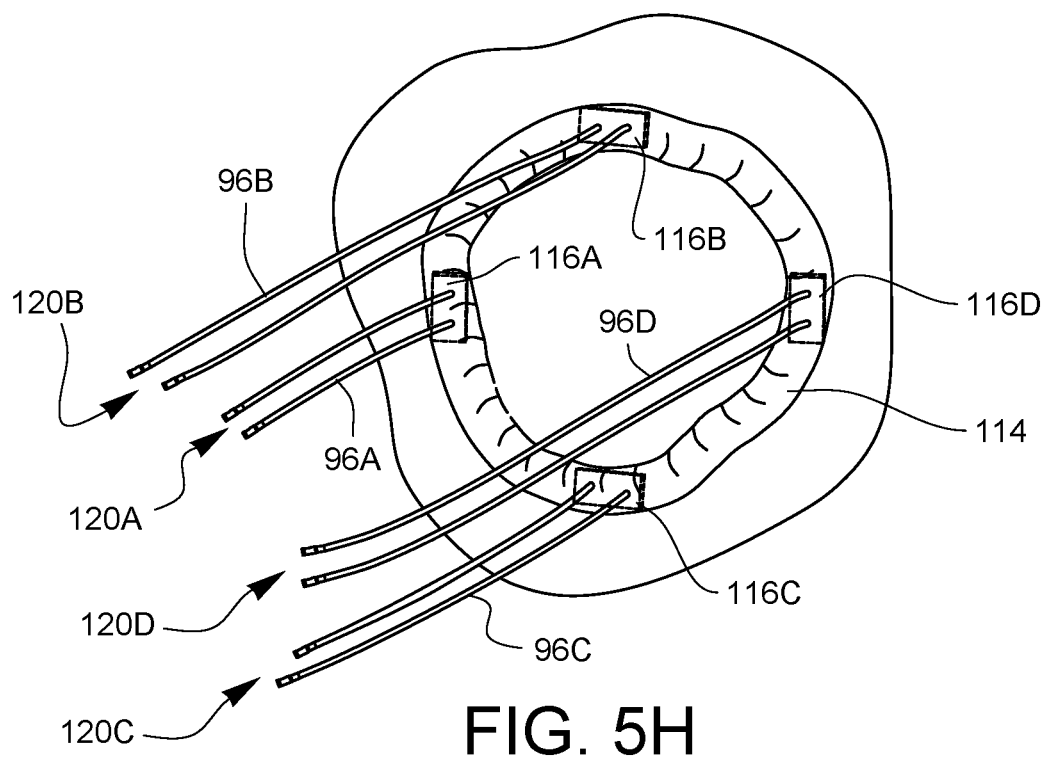
FIG. 5H illustrates the result of having performed the process of FIGS. 5A-5G four times.

The ferrules 88, 90 on the ends of the suture 96 can be released or otherwise removed. Another suture can be loaded into the device, and the process can be repeated around the annulus 114 as many times as desired by the surgeon. As a simple example, FIG. 5H illustrates the result of having performed the process four times with the device 48. Four sutures 96A, 96B, 96C, 96D have been placed in desired locations through the annulus 114. In practice, this process can be used for any number of sutures. The four sutures illustrated here are just for the convenience of explanation. Each pair of ferruled suture ends 120A, 120B, 120C, and 120D may be held off to the side and tracked until all of the sutures have been placed in the annulus.

At this point, it is desirable to sew each pair of sutures ends 120A, 120B, 120C, and 120D through a sewing cuff of a replacement valve. The suturing device 48 which was used to place the first sets of stitches in the annulus 114 can be used to place the stitches in the replacement valve sewing cuff. However, it may be difficult to reliably position a stitch on the sewing cuff with just the suturing device. Accordingly, a suturing backstop may be coupled to the suturing device tip to facilitate suturing of the sewing cuff.

Figure 6A:
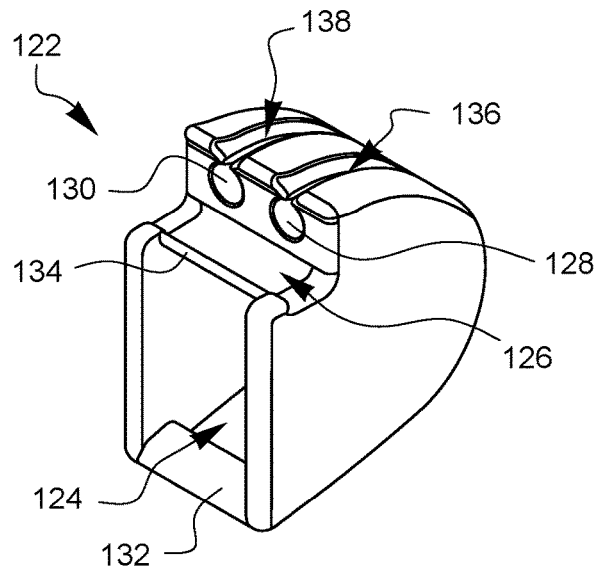
FIG. 6A is a front-right-top perspective view of one embodiment of a suturing backstop.
Figure 6B:
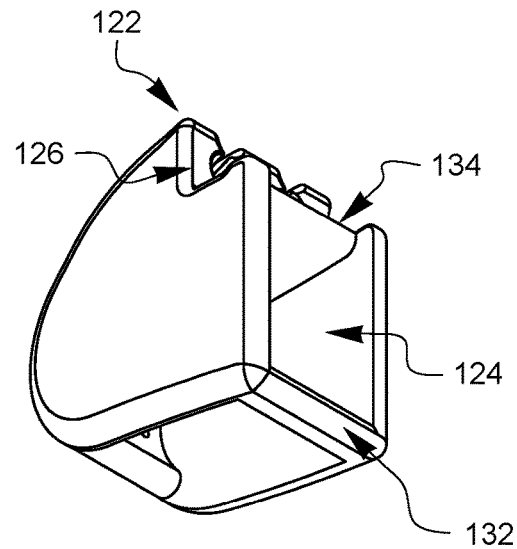
FIG. 6B is a front-left-bottom perspective view of the suturing backstop from FIG. 6A.
Figure 6C:
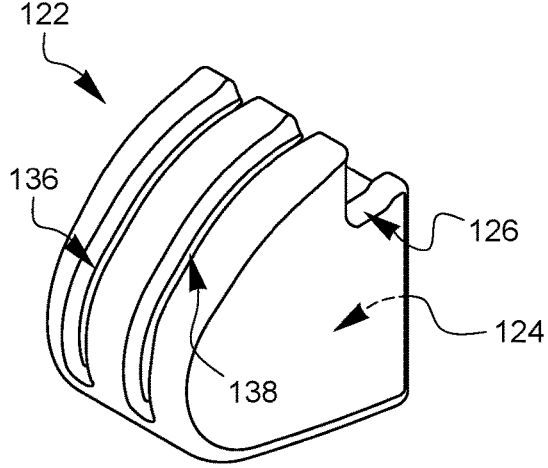
FIG. 6C is a back-left-top perspective view of the suturing backstop from FIG. 6A.
Figure 6D:
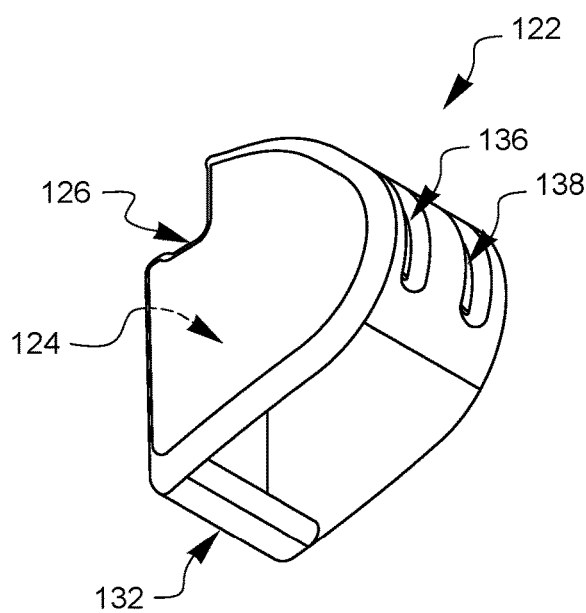
FIG. 6D is a back-right-bottom perspective view of the suturing backstop from FIG. 6A.

FIG. 6A is a front-right-top perspective view of one embodiment of a suturing backstop 122. FIG. 6B is a front-left-bottom perspective view of the suturing backstop 122 from FIG. 6A. FIG. 6C is a back-left-top perspective view of the suturing backstop 122 from FIG. 6A. FIG. 6D is a back-right-bottom perspective view of the suturing backstop 122 from FIG. 6A. FIGS. 7A, 7B, 7C, 7D, 7E, and 7F are front, left, right, back, top, and bottom elevational views of the suturing backstop 122 from FIG. 6A.

The suturing backstop 122 has a suturing device receiver 124 configured to receive at least a portion of a tissue bite area of a suturing device. The suturing device receiver 124 also has a sewing cuff receptacle 126. In this embodiment, the sewing cuff receptacle 126 is contoured in the bottom middle to help accommodate a round sewing cuff. Other embodiments may have other shapes to help support and position one or more different kinds of sewing cuffs. In this embodiment, the suturing backstop 122 also has first and second needle guides 128, 130 adjacent the sewing cuff receptacle 126. Other embodiments may have fewer or more needle guides, depending on how many needles are in the suturing device which the suturing backstop 122 will be used with. Each of the needle guides 128, 130 are preferably funnel-like, starting from a wider opening near the sewing cuff receptacle 126 and narrowing as the guide moves away from the sewing cuff receptacle 126. This narrowing or funneling configuration can help ensure needles are steered back into alignment with ferrules in their ferrule receivers, even when the needles may have initially been pushed off their track from passage through a sewing cuff placed in the sewing cuff receptacle. Depending on the embodiment, the needle guides may be configured to steer a needle tip which is travelling on a curved path or a straight path.

The suturing backstop 122 also has one or more alignment stops 132, 134 which are configured to position the tissue bite area of a suturing device within the suturing device receiver 124 such that when a needle from the suturing device is extended from a retracted position to an engaged position, the needle passes through the sewing cuff receptacle 126 and through a corresponding one of the one or more needle guides 128, 130. It should be noted that when we describe a needle as "passing through the sewing cuff receptacle", this refers to the needle passing through an area adjacent to the sewing cuff receptacle where a sewing cuff would be supported by the sewing cuff receptacle.

The embodiment of FIGS. 6A-6D and 7A-7F also has a first suture access slot 136 in communication with the first needle guide 128. There is also a second suture access slot 138 in communication with the second needle guide 130. These suture access slots 136, 138 allow a ferrule on the end of a suture to be loaded into the ferrule holders of the portion of the suturing device which might be covered and otherwise inaccessible while the suture backstop 122 is attached to the suturing device tip. The ferrules can be fed through the needle guides by holding the suture coupled to the ferrule. The suture can then be moved to position the ferrules in the ferrule holders by pulling the suture back down along the suture access slots 136, 138. Although the suture access slots 136, 138 are not strictly necessary, they do avoid situations where the backstop 122 has to be removed between each ferrule loading.

Figure 8:
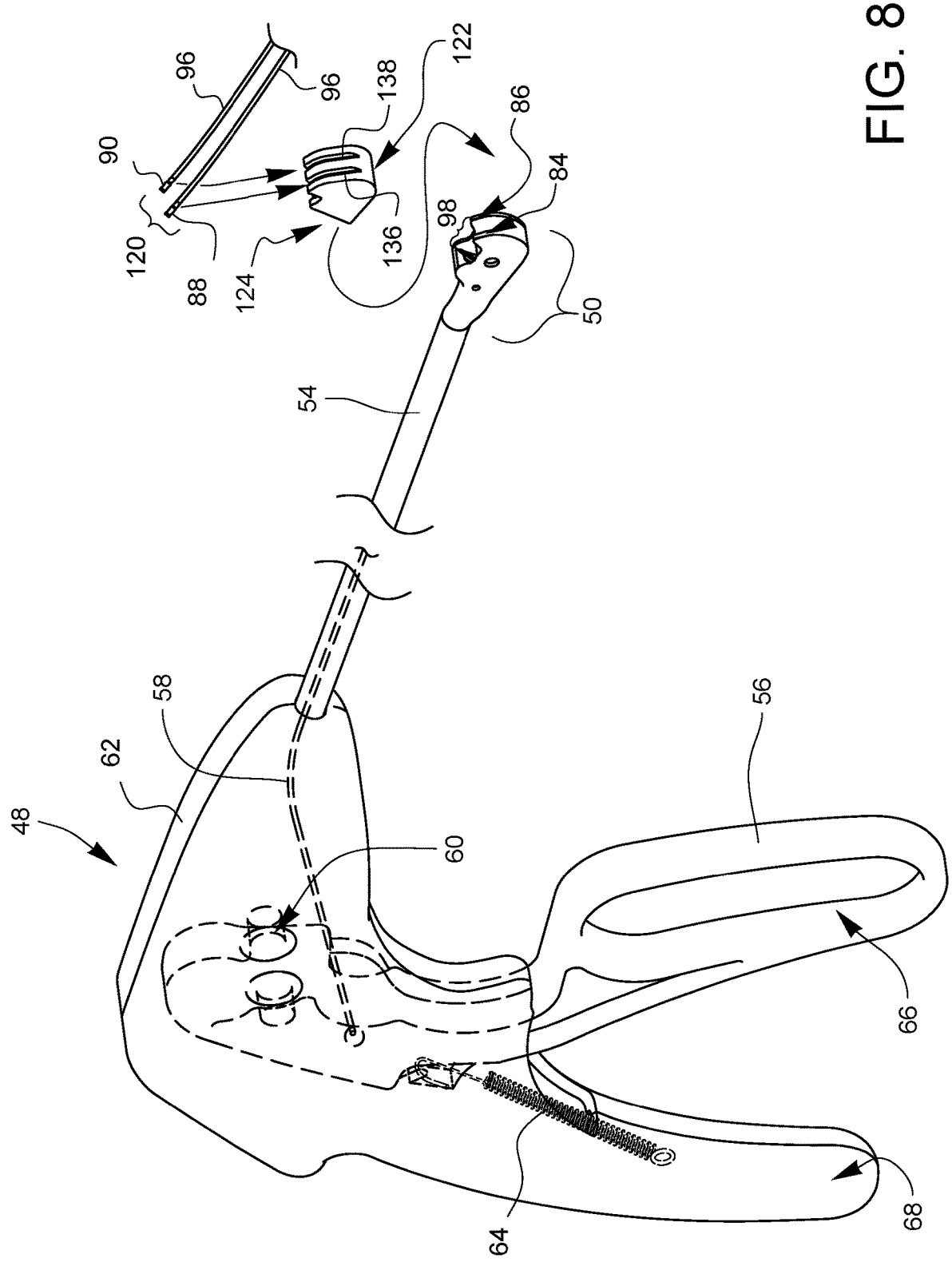
FIG. 8 illustrates a surgical situation, for example, one where there are pairs of suture ends from sutures which have been placed in tissue, such as, for example, as was shown in FIG. 5H.

FIG. 8 illustrates a surgical situation. Primarily, it takes over from the previous situation of FIG. 5H. Recall that a number of pairs of suture ends had been collected after each associated suture had been stitched through an aortic annulus. FIG. 8 illustrates one such pair of suture ends 120 from suture 96. Ferrules 88, 90 are coupled to the suture ends. We also have a surgical suturing device 48, the details of which have been discussed above. Furthermore, we have a suturing backstop 122, the features of which have also been discussed above. The suturing device receiver 124 is placed around the device tip 50 so that a portion of the tissue bite area 98 is received by the suturing device receiver 124. The ferrules 88, 90 are placed into the needle guides (not visible in this view) and the suture 96 is pulled back through the suture access slots 136, 138 to seat the ferrules 88, 90 in their respective ferrule holders 84, 86 in the device tip 50.

Figure 9A:
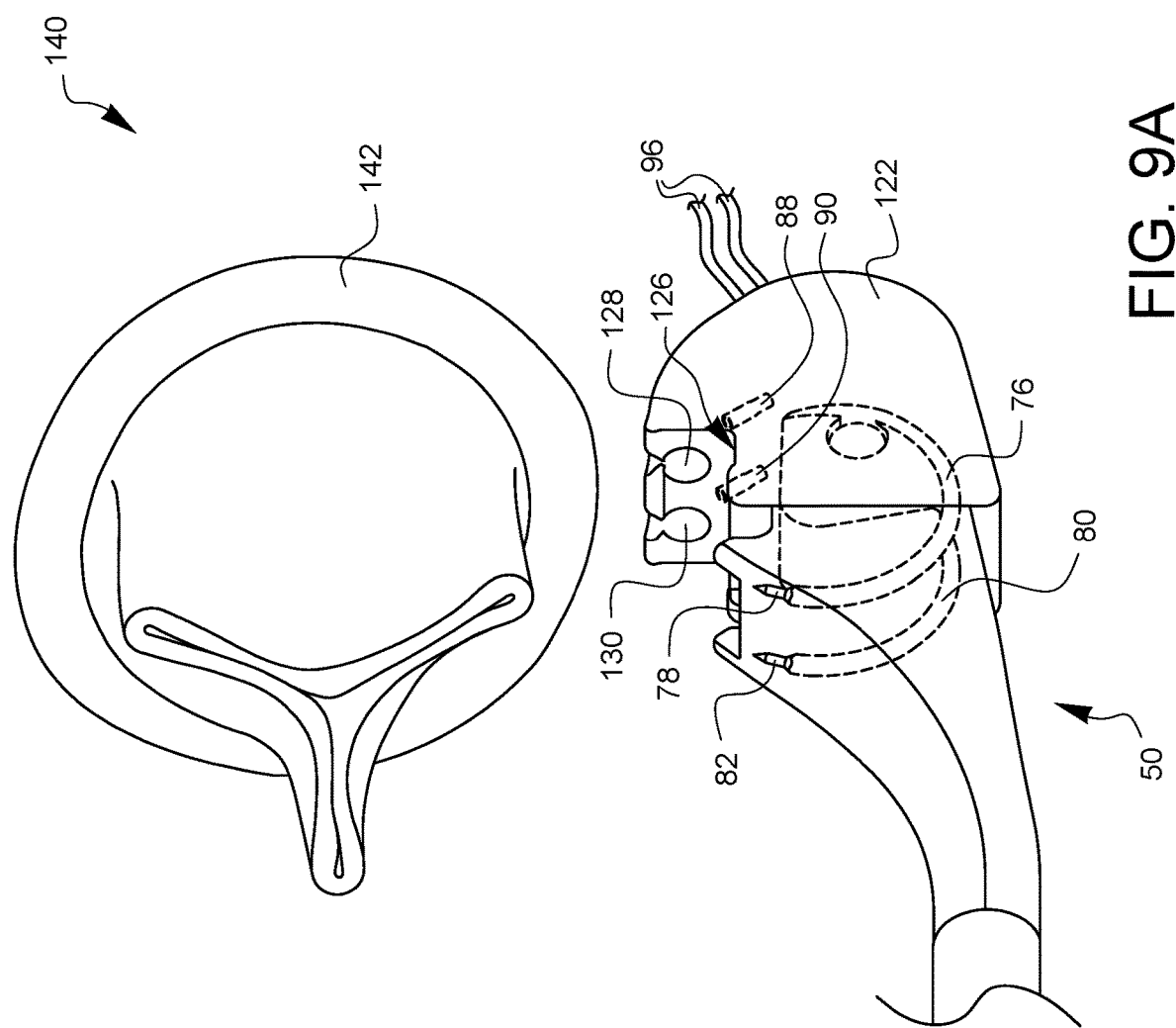
FIGS. 9A-9E illustrate a method of using an embodiment of a suturing backstop with a surgical suturing device to place suture stitches through a suturing cuff of a prosthetic device.
Figure 9B:
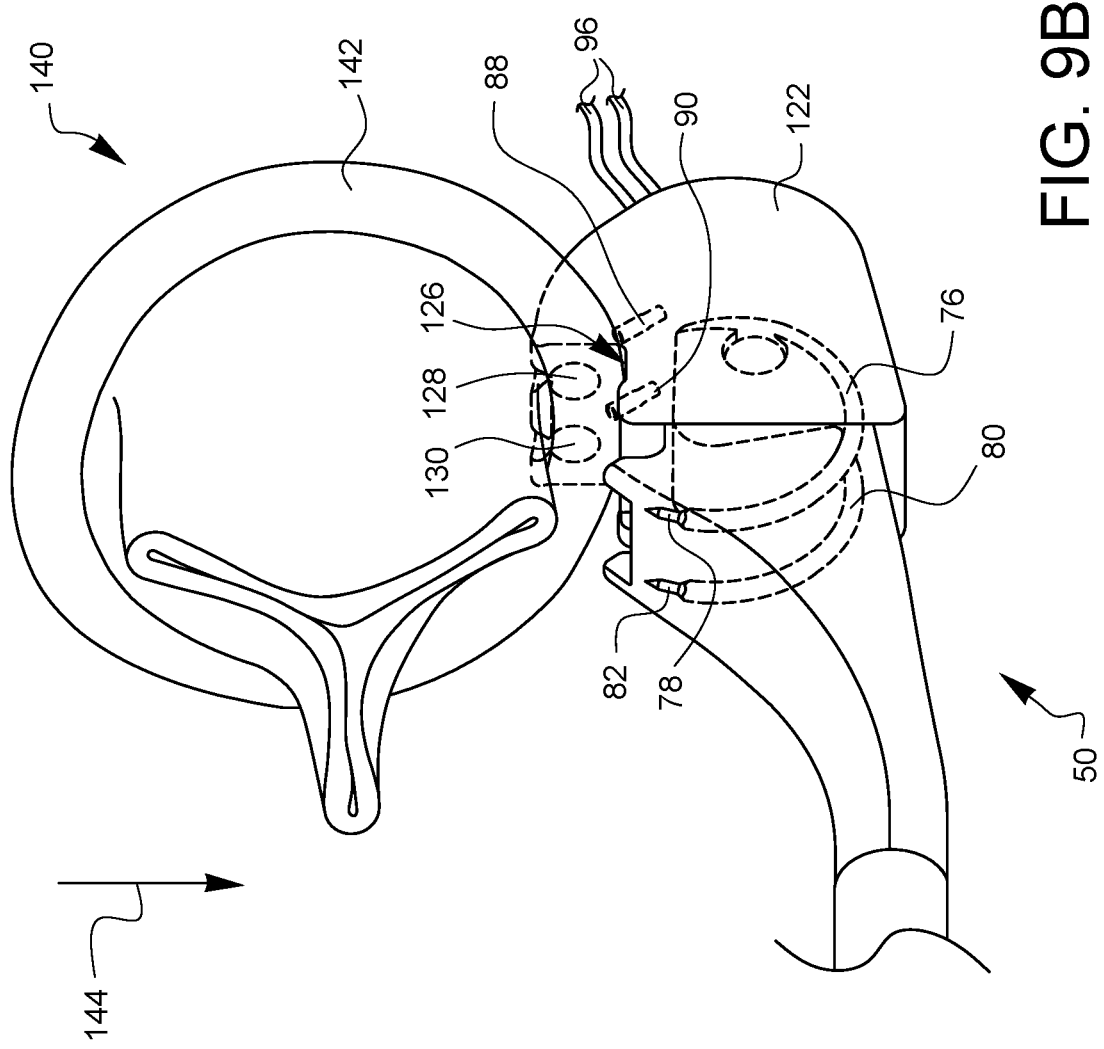

FIG. 9A illustrates the suturing device tip 50 inserted into the suture backstop 122 with the ferrules 88, 90 in-place in the ferrule holders (obscured by the suture backstop 122). A prosthetic valve 140 with a sewing cuff 142 is also available, but not yet engaging the suture backstop 122. As illustrated in FIG. 9B, sewing cuff 142 of the prosthetic valve 140 is set down 144 into the sewing cuff receptacle 126 of the suturing backstop 122. The sewing cuff receptacle 126 may be sized to position the sewing cuff 142 at a desired height relative to the needle guides 128, 130, thereby making it easier for surgeons to properly position the valve 140 for suturing.

Figure 9C:
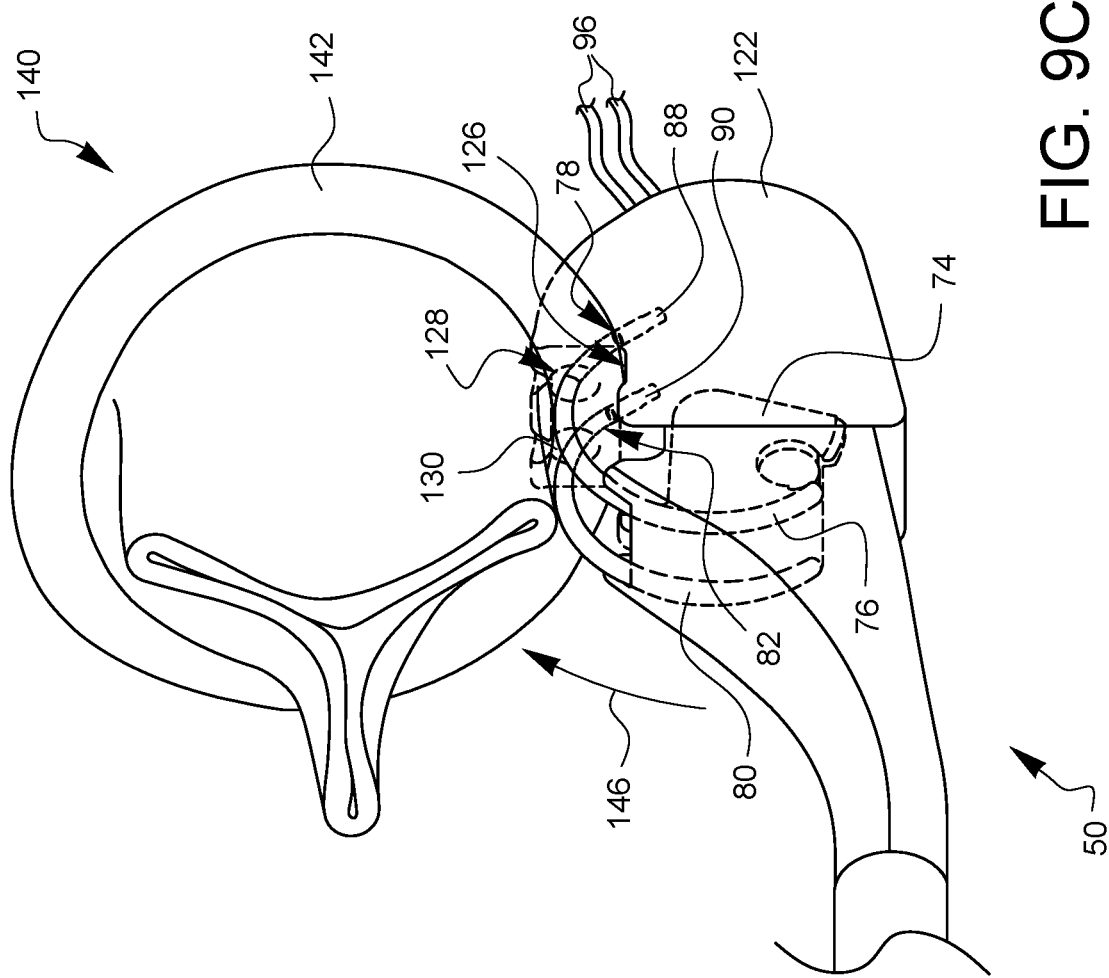

As shown in FIG. 9C, the needle 74 may be engaged (in this example, rotated 146 in a first direction) so that the needle tips 78, 82 each pass through the sewing cuff 142 as it is held in the sewing cuff receptacle 126, through their corresponding needle guides 128, 130, and into contact and coupling with their respective ferrules 88, 90. As mentioned earlier, the needle guides 128, 130 serve to ensure that the needle moves back into alignment with the ferrules if necessary as a result of possible deflection from the sewing cuff 142.

Figure 9D:
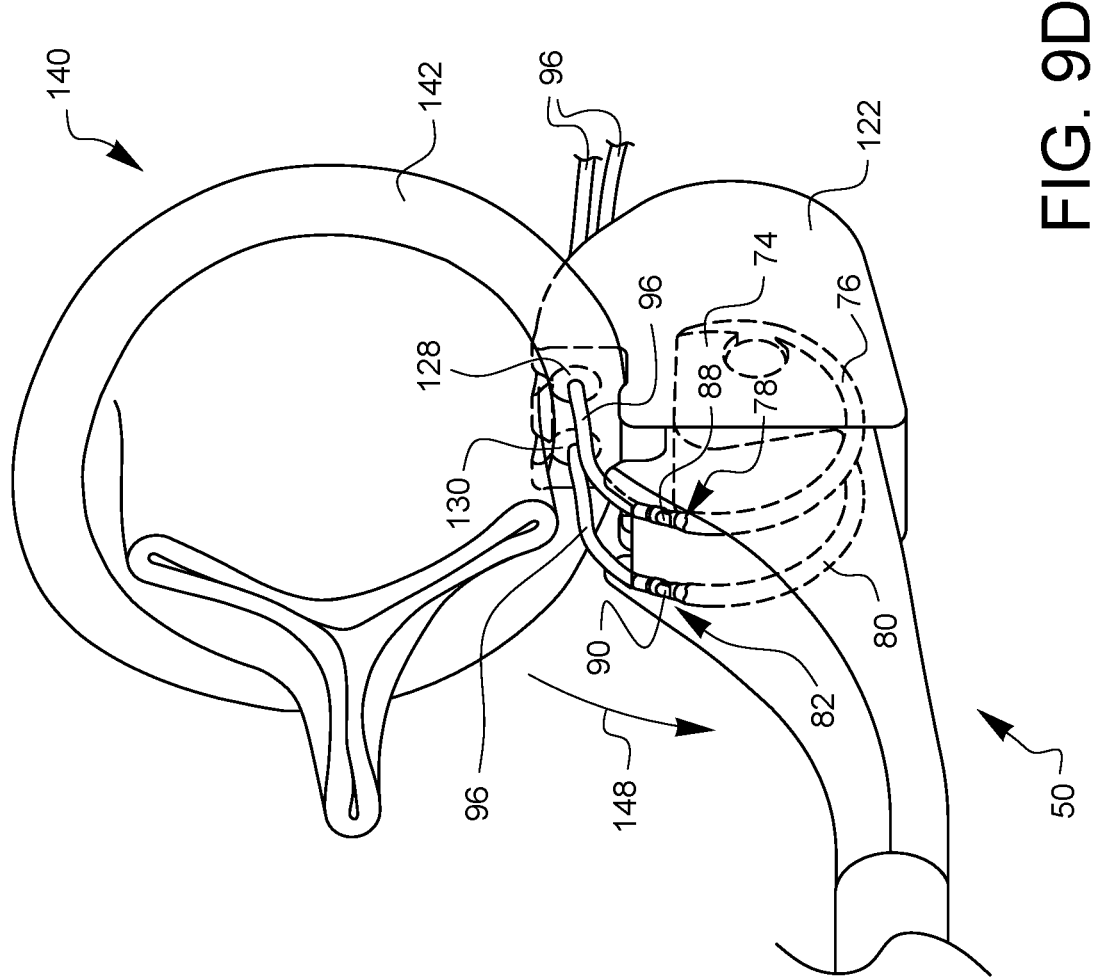

As shown in FIG. 9D, the needle 74 may be retracted (in this example, rotated 148 in a second direction opposite the first) so that the needle tips 78, 82 each pull back through the needle guides 128, 130, back through the sewing cuff 142 which is held in the sewing cuff receptacle 126, and into a retracted position. Since the ferrules 88, 90 are coupled to the needle tips 78, 82, the ferrules 88, 90 and the suture 96 attached to them is also pulled out through the sewing cuff 142.

Figure 9E:
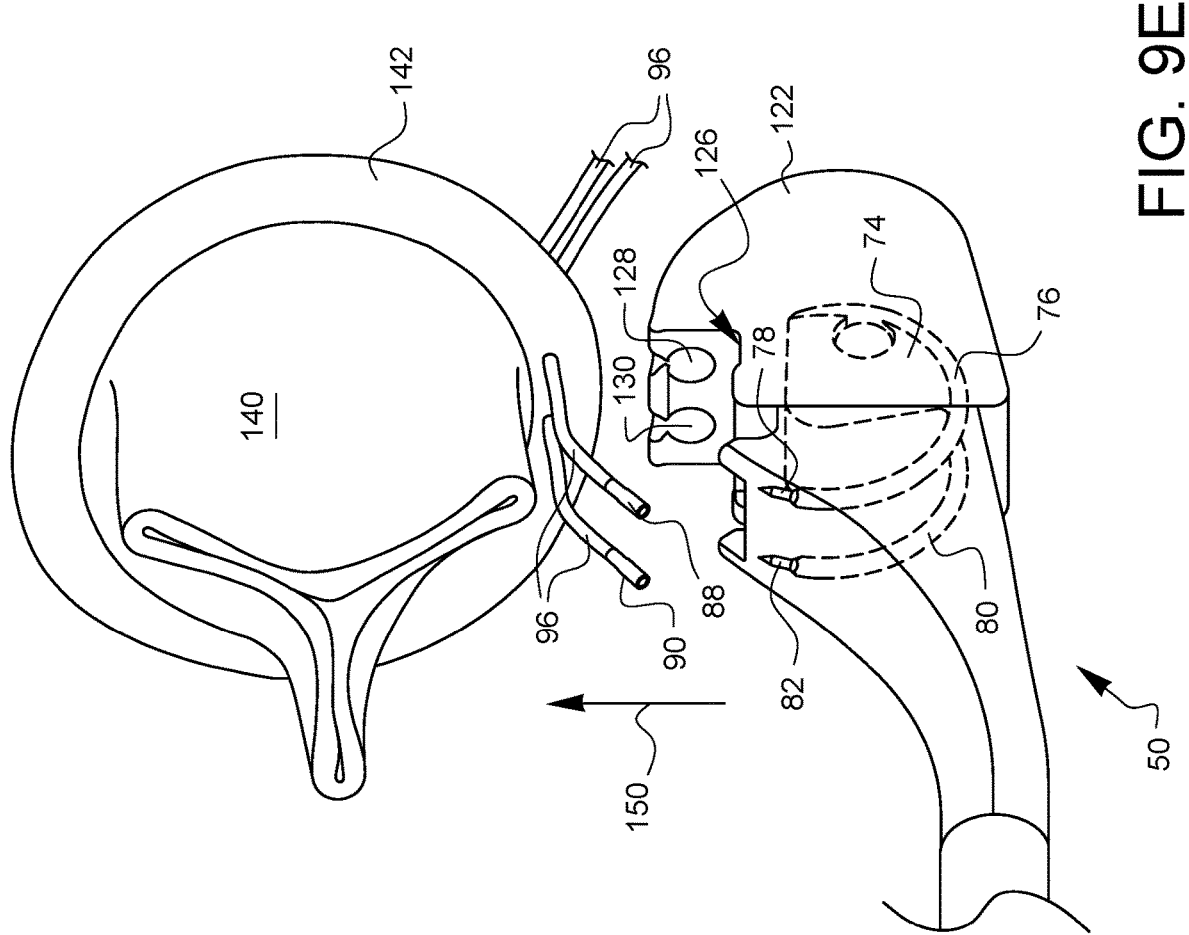

As shown in FIG. 9E, the ferrules 88, 90 may be released from the suturing device tip 50 in a variety of manners known to those skilled in the art. The prosthetic valve 140 may then be removed 150 from the sewing cuff receptacle 126. Ferrules from a new pair of suture ends may be loaded into the suturing device tip 50 through the needle guides 128, 130 as done before, and the valve may be rotated to place a different portion of the sewing cuff 142 into the sewing cuff receptacle 126 while the process of FIGS. 9A-9E is repeated as many times as necessary to stitch all suture pairs 120 through the sewing cuff 142. The suturing backstop efficiently enables a surgeon to place these suture stitches with even spacing.

Figure 10A:
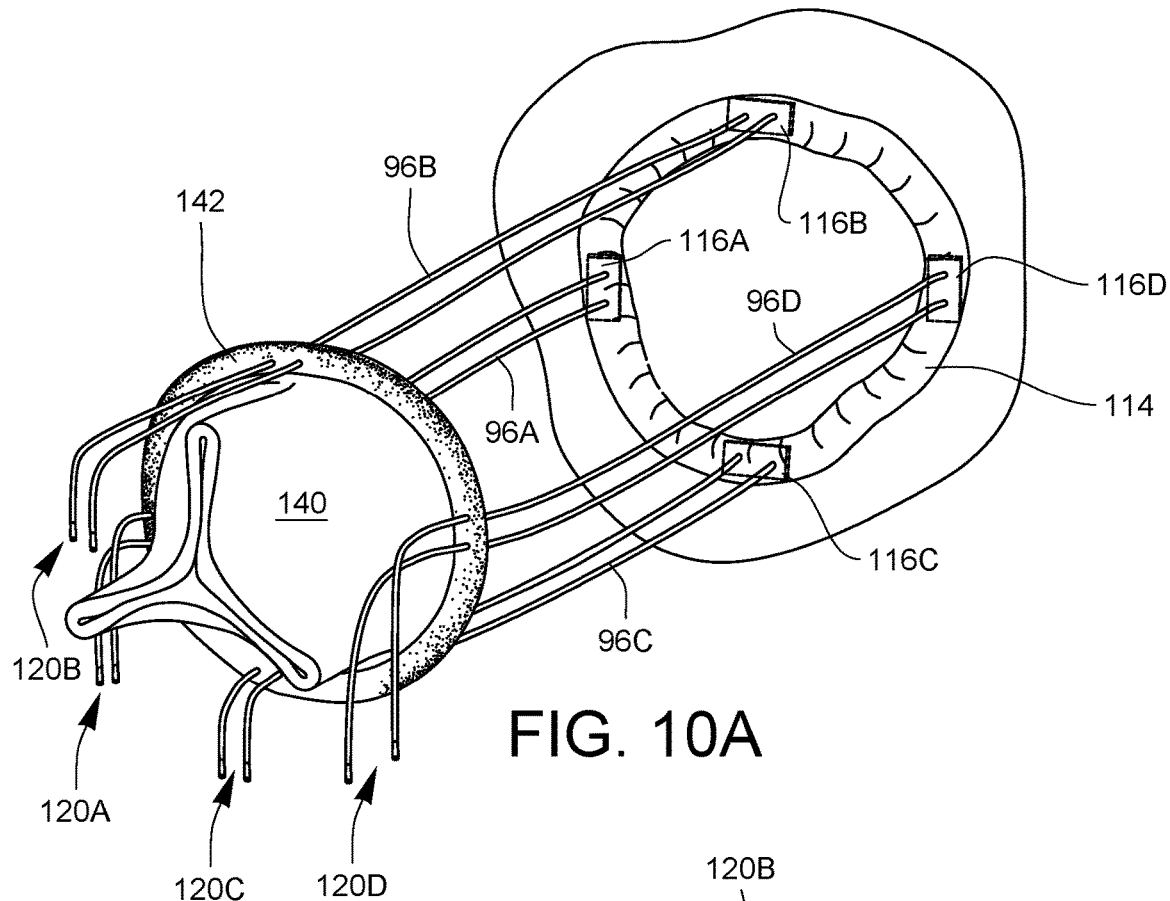
FIG. 10A illustrates a prosthetic valve after four pairs of suture ends have been stitched through the sewing cuff using the suturing backstop and the procedure of FIGS. 9A-9E.
Figure 10B:
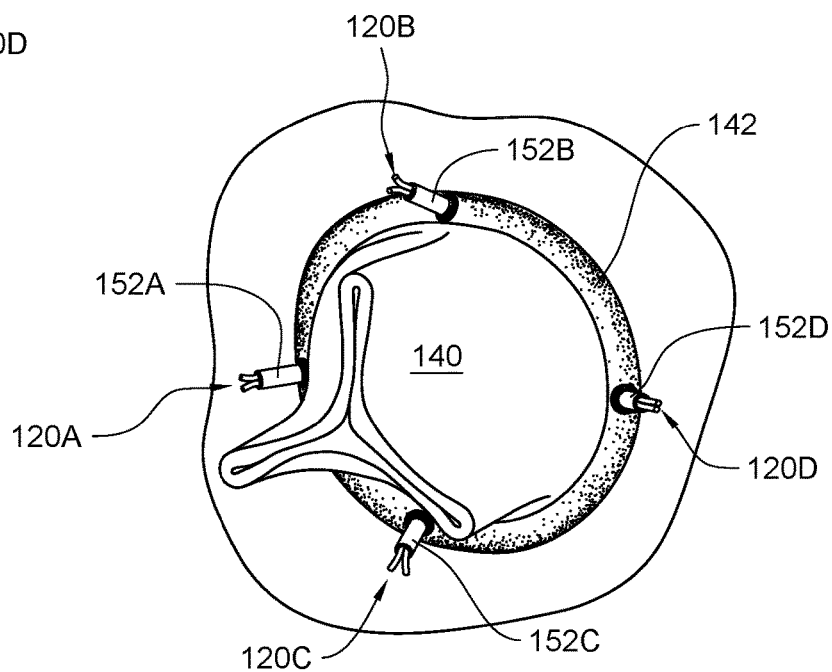
FIG. 10B shows the suture ends of FIG. 10A having been secured with mechanical fasteners.

FIG. 10A illustrates a prosthetic valve after four pairs of suture ends 120A, 120B, 120C, and 120D have been stitched through the sewing cuff using the suturing backstop and the procedure of FIGS. 9A-9E. The ferrules may be removed from the suture ends, and the suture ends can then be secured using a variety of methods and devices. FIG. 10B shows the suture ends 120A-120D having been secured with corresponding mechanical fasteners 152A-152D such as the COR-KNOT® fastener from LSI Solutions, Inc. of Victor, N.Y. (www.ldisolutions.com).

Various advantages of a suturing backstop for minimally invasive surgery have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A suturing backstop, comprising:
    a suturing device receiver configured to receive at least a portion of a tissue bite area of a suturing device;
    a sewing cuff receptacle;
    one or more needle guides adjacent the sewing cuff receptacle; and
    one or more alignment stops proximal to the sewing cuff receptacle and configured to position said portion of the tissue bite area within the suturing device receiver such that when a needle from the suturing device is extended from a retracted to an engaged position, the needle passes through the sewing cuff receptacle and through a corresponding one of the one or more needle guides;
    wherein the suturing backstop is configured to be removable from the suturing device.

2. The suturing backstop of claim 1, wherein the one or more needle guides are sized to allow a ferrule to pass therethrough.

3. The suturing backstop of claim 1, further comprising one or more corresponding suture access slots for and in communication with each of the one or more needle alignment guides.

4. The suturing backstop of claim 1, wherein the one or more needle guides comprise a funnel-like shape.

5. The suturing device of claim 1, wherein the sewing cuff receptacle is contoured to accommodate a round sewing cuff.

6. The suturing device of claim 1, wherein the one or more needle guides are configured to steer a needle tip which is travelling on a curved path.

7. The suturing device of claim 1, wherein the one or more needle guides are configured to steer a needle tip which is travelling on a substantially straight path.

* * * * *